United States Patent [19]

Nakano et al.

[11] Patent Number: 5,340,591
[45] Date of Patent: Aug. 23, 1994

[54] METHOD OF PRODUCING A SOLID DISPERSION OF THE SPARINGLY WATER-SOLUBLE DRUG, NILVADIPINE

[75] Inventors: Minoru Nakano; Toshinobu Uemura, both of Kishiwada; Shinichi Morizane, Osaka; Kiyoshi Okuda, Ohtsu; Keiko Nakata, Ibaraki, all of Japan

[73] Assignee: Fujisawa Pharmaceutical Co., Ltd., Osaka, Japan

[21] Appl. No.: 300

[22] Filed: Jan. 4, 1993

[30] Foreign Application Priority Data

Jan. 24, 1992 [JP] Japan .................................. 4-010796

[51] Int. Cl.$^5$ ....................... A61K 9/50; A61K 31/44; A61K 47/00
[52] U.S. Cl. ..................................... 424/499; 514/344; 514/772.7; 514/774; 514/781; 514/782
[58] Field of Search ...................... 424/499; 514/772.7, 514/781, 344, 774, 782

[56] References Cited

U.S. PATENT DOCUMENTS

| | | | |
|---|---|---|---|
| 2,540,253 | 2/1951 | Gakenheimer | 167/57 |
| 2,778,768 | 1/1957 | Brown et al. | 167/42 |
| 2,980,589 | 4/1961 | de Grunigen | 167/82 |
| 3,290,218 | 12/1966 | de Jong | 167/82 |
| 3,692,896 | 9/1972 | Tsumura et al. | 424/78 |
| 4,338,322 | 7/1982 | Sato | 424/266 |
| 4,654,206 | 3/1987 | Okuda et al. | 424/480 |

FOREIGN PATENT DOCUMENTS

| | | |
|---|---|---|
| 54-29565 | 3/1979 | Japan . |
| 2145332A | 3/1985 | United Kingdom . |

OTHER PUBLICATIONS

Database WPIL, Derwent Publications Ltd., AM 85-28036545, & JP-A-60 190 723, Sep. 28, 1985.
Patent Abstracts of Japan, vol. 010, No. 185 (C-357), Jun. 27, 1986, JP-A-61 033 128, Feb. 17, 1986.
Patent Abstracts of Japan, vol. 015, No. 048 (C-0802), Feb. 5, 1991, JP-A-22 79 631, Nov. 15, 1990.
Patent Abstracts of Japan, vol. 010, No. 043 (C-329), Feb. 20, 1986, JP-A-60 190 723, Sep. 28, 1985.
Patent Abstracts of Japan, vol. 010, No. 230 (C-365), Aug. 9, 1986, JP-A-61 063 614, Apr. 1, 1986.
International Journal of Pharmaceutics, 47 (1988) 51-66, E. Sjokvist, et al., "Physicochemical Aspects of Drug Release. VI. Drug Dissolution Rate From Solid Particulate Dispersions and the Importance of Carrier and Drug Particle Properties".
Chemical & Pharmaceutical Bulletin, vol. 9, No. 11, 1961, K. Sekiguchi, et al., "Studies on Absorption of Eutectic Mixture. I. a Comparison of the Behavior of Eutecic Mixture of Sulfathiazole and that of Ordinary Sulfathiazole in Man".
Chemical Abstracts 103:59329n, 1985, Okuda et al.
Chemical Abstracts 115:189815b, 1991, Ueda et al.

*Primary Examiner*—Marianne M. Cintins
*Assistant Examiner*—Minna Moezie
*Attorney, Agent, or Firm*—Oblon, Spivak, McClelland, Maier & Neustadt

[57] ABSTRACT

A solid dispersion and a method of producing a solid dispersion of a sparingly water-soluble drug characterized by mixing the sparingly water-soluble drug and a water-soluble polymer at a temperature where neither the water-soluble drug nor water-soluble polymer is melted.

4 Claims, No Drawings

METHOD OF PRODUCING A SOLID DISPERSION OF THE SPARINGLY WATER-SOLUBLE DRUG, NILVADIPINE

This invention relates to a novel method of producing a solid dispersion, a solid dispersion as prepared by the method, and an oral preparation comprising the same. This invention is utilized in the medical field.

In designing a pharmaceutical preparation for oral administration, it is generally considered important, from efficacy and safety points of view, to maximize the bioavailability of the active ingredient.

The solubility of drugs is generally mentioned as an important factor in the bioavailability of pharmaceutical products and much research has been undertaken into the relationship between solubility and gastrointestinal absorption. Particularly regarding a sparingly water-soluble drug, it is generally acknowledged that the rate of dissolution is the rate-determining step of absorption.

While a variety of pharmaceutical techniques are known for improving the solubility of sparingly water-soluble drugs, the technology which deserves special mention is one concerning solid dispersions.

This is defined as a technology for dispersing a drug monomolecularly in a solid state into an inert carrier. The technology specifically includes a solvent process, a fusion process, and a mixed-grinding process (mechanochemical process).

The solvent process either comprises dissolving a sparingly water-soluble drug and a water-soluble polymer, i.e. the carrier, in an organic solvent capable of dissolving both and removing the solvent by evaporation or comprises dissolving the drug in an organic solvent, dispersing the solution in the carrier and removing the solvent by evaporation to provide the desired solid dispersion.

The fusion process either comprises heating the drug and the water-soluble polymer together by utilizing the phenomenon of melting point depression, cooling the melt to solidify and pulverizing the resulting solid to provide the desired solid dispersion [Chem. Pharm. Bull. 9, 866 (1961)] or comprises dissolving the drug in a comparatively low-melting water-soluble polymer under heating, cooling the resulting solution to solidify and pulverizing the solid to provide the desired solid dispersion [Int. J. Pharm, 47, 51 (1988)].

The mixed-grinding (mechanochemical) technology, in which the sparingly water-soluble drug and the water-soluble polymer are mix-ground or roll-mixed without heating to thereby make the drug amorphous and thereby disperse it evenly is also known (Japanese Patent Publication No. 29565/1979 and No. 7811/1983).

The term 'mechanochemical' used here signifies the phenomenon that a mechanical energy (compression, shear, friction) alters the physicochemical properties of a substance. It is considered that here various factors arising from mechanical manipulation, such as lattice defect or lattice modulation, increases in specific surface area and surface energy and so on, enhances the activity of the solid phase to encourage transition of the drug to an amorphous state and, hence, dispersion of the drug in this amorphous state into the carrier.

Among these various known technologies for the production of a solid dispersion, the solvent process is advantageous in that the resulting solid dispersion is very satisfactory in the solubility and bioavailability of the sparingly water-soluble drug but has the disadvantage of high production cost associated with the inevitable use of an organic solvent in a large quantity.

On the other hand, the fusion process does not require an organic solvent but since the melting of the sparingly water-soluble drug and water-soluble polymer entails a cooling step (cooling of the viscous matter) and a solid pulverizing step, a time-consuming multiple-stage operation is required.

Furthermore, the solid dispersion obtained by the mixed-grinding process is not fully satisfactory in the solubility and bioavailability of the sparingly water-soluble drug.

After much research to overcome the above drawbacks of the prior art technologies, the inventors of this invention conceptualizing the formation of a solid dispersion as the solid-to-solid interaction between an sparingly water-soluble drug and a water-soluble polymer and exploring various ways to promote that interaction, discovered that by mechanical preactivation through the unit operation of mixing in combination with thermal treatment, the transition of the sparingly water-soluble drug to an amorphous state and the dispersion of the drug in this amorphous state into the carrier can be successfully promoted.

It was, thus, found that only by the simple process which, quite unlike the conventional production processes, comprises mixing a sparingly water-soluble drug and a water-soluble polymer together under no more than the usual agitation force with heating within the temperature region not melting them, instead of heating the system to the extent that the two materials are melted, the sparingly water-soluble drug can be made amorphous to thereby yield a solid dispersion insuring very high solubility and bioavailability which have never been achieved by any dry process heretofore known.

The technology of this invention for the production of a solid dispersion of a sparingly water-soluble drug is characterized by mixing the sparingly water-soluble drug and a water-soluble polymer together under heating at a temperature not melting them. The inventors named the technology 'thermal-mechanochemical process'.

The term 'sparingly water-soluble drug' is used herein to mean any drug with poor water solubility and resulting poor bioavailability after oral administration, thus specifically meaning phenacetin, phenytoin, digitoxin, nifedipine, nilvadipine, diazepam, griseofulvin and chloramphenicol, or the like.

The water-soluble polymer for use in this invention includes cellulose derivatives (for example, methylcellulose, ethylcellulose, hydroxyethylcellulose, hYdroxypropylcellulose, hydroxypropylmethylcellulose, carboxymethylcellulose, etc.), polyvinylpyrrolidone, polyvinyl alcohol, gum arabic, dextrin and gelation, or the like.

The ratio of the sparingly water-soluble drug to the water-soluble polymer in the solid dispersion of this invention can be selected according to the species of sparingly water-soluble drug and of water-soluble polymer. Thus, the ratio may be generally 1:0.5 through 1:10 by weight and preferably 1:1 through 1:5 by weight.

In the production method of this invention for such a solid dispersion, there can be employed a variety of additives which are commonly used in the pharmaceutical field, such as an excipient (e.g. crystalline cellulose, corn starch, D-mannitol, lactose, etc.) and a disintegrator (e.g. low-substituted hydroxypropylcellulose, hydroxypropylstarch, sodium starch-glycolate, etc.) in appropriate proportions in addition to the sparingly water-soluble drug and water-soluble polymer.

The method of the invention for the production of a solid dispersion comprises charging a mixing device, such as a universal mixer, a high-speed stir-granulator or a kneader, with the sparingly water-soluble drug, water-soluble polymer, and said excipient, disintegrator and other additives and mixing them together under heating.

For small-scale production, the above ingredients can be placed in a beaker or the like and mixed under heating.

The heating temperature should be lower than the lower of the melting point of the sparingly water-soluble drug and that of the water-soluble polymer and is preferably lower by 5° to 50° C., more preferably by 5° to 25° C., than said lower melting point.

The mixing time is not critical but is generally 0.5 to 10 hours.

Thermal analysis of the solid dispersions obtained by the method of the invention in the Examples given hereinafter using differential scanning calorimetry revealed disappearance of the endothermic peak of the sparingly water-soluble drug, indicating that the sparingly water-soluble drug was made amorphous to give a solid dispersion.

The solid dispersion thus obtained in accordance with this invention is a powder and while this powder can be used as it is for oral administration, it can be formulated into fine granules or granules using a roller compacter, etc. or processed into tablets, capsules or the like in the conventional manner for oral administration.

Test Example 1 Solubility Test

Test Samples

1. The sample obtained in Example 1 given hereinafter
2. The sample obtained in Example 3 given hereinafter
3. The sample obtained in Example 4 given hereinafter
4. The sample obtained in Production Example 1 given hereinafter
5. The sample obtained in Production Example 2 given hereinafter
6. The sample obtained in Production Example 3 given hereinafter

[Solubility of nilvadipine bulk substance: 1.3 μg/ml (J.P., 1st fluid), 1.0 μg/ml (J.P, 2nd fluid)]

Test Method

The dissolution test was carried out in accordance with Dissolution Test (Paddle method, 100 rpm, 1st fluid 900 ml, 37° C.) of Japanese Pharmacopoeia (J.P.) XII.

The sample size was invariably 20 mg nilvadipine equivalent and the amount of dissolution at 2 hours after initiation of the test was adopted.

RESULTS

TABLE 1

| Test sample | Amount of dissolution of nilvadipine (μg/ml) |
| --- | --- |
| 1 | 21.1 |
| 2 | 14.9 |
| 3 | 17.3 |
| 4 | 5.3 |
| 5 | 5.6 |
| 6 | 21.3 |

Test Example 2 Solubility Test

Test Samples

7. The sample obtained in Example 5 given hereinafter
8. The sample obtained in Production Example 5 given hereinafter

[Solubility of nifedipine bulk substance: 12 μg/ml distilled water]

TEST METHOD

The dissolution test was carried out in accordance with Dissolution Test (Paddle method, 100 rpm, 1st fluid 900 ml, 37° C.) of Japanese Pharmacopoeia (J.P.) XII.

The sample size was 90 mg nifedipine equivalent and the amount of dissolution at 2 hours after initiation of the test was adopted.

RESULTS

TABLE 2

| Test sample | Amount of dissolution of nifedipine (μg/ml) |
| --- | --- |
| 7 | 56.3 |
| 8 | 9.8 |

The results of Test Examples 1 and 2 indicate that in the solubility of sparingly water-soluble drugs, the solid dispersion produced by the method of this invention is superior to the solid dispersion obtainable by the roll-mixing process or that obtainable by the ball mill mixed-grinding method and is comparable to the solid dispersion obtainable by the solvent process.

Test Example 3 Bioavailability Test

Test Samples

9. The sample obtained in Example 2 given hereinafter
10. The sample obtained in Production Example 4 given hereinafter

TEST METHOD

Six beagle dogs (body weights 8–11 kg) fasted overnight were orally dosed with one tablet each of the above test samples (containing 4 mg of nilvadipine) in the crossover design and using a gas chromatograph equipped with ECD, the plasma nilvadipine concentration was determined at 0.5, 1, 1.5, 2, 4, 6 and 8 hours after administration.

RESULTS

TABLE 3

| Test sample | Plasma concentration (ng/ml) | | | | | | | AUC (ng/ml · hr) |
| --- | --- | --- | --- | --- | --- | --- | --- | --- |
| | 0.5 hr | 1 hr | 1.5 hr | 2 hr | 4 hr | 6 hr | 8 hr | |
| 9 | 46.0 ± 11.7 | 49.4 ± 14.2 | 41.2 ± 17.0 | 36.5 ± 13.3 | 25.1 ± 9.5 | 22.2 ± 9.5 | 21.8 ± 7.1 | 230.2 ± 73.2 |

TABLE 3-continued

| Test | Plasma concentration (ng/ml) | | | | | | | AUC |
|---|---|---|---|---|---|---|---|---|
| sample | 0.5 hr | 1 hr | 1.5 hr | 2 hr | 4 hr | 6 hr | 8 hr | (ng/ml · hr) |
| 10 | 48.9 ± 20.0 | 57.1 ± 3.2 | 43.3 ± 7.5 | 36.6 ± 8.4 | 26.7 ± 9.0 | 23.8 ± 9.2 | 22.0 ± 9.3 | 243.4 ± 60.7 |

(Mean ± SD of 6 dogs)

The above results indicate that the tablet containing the solid dispersion produced by the method of this invention is comparable to the tablet containing the solid dispersion obtainable by the solvent process in the absorption (bioavailability) of nilvadipine after oral administration.

Compared with the conventional solvent process, the method of this invention for the production of a solid dispersion is conducive to cost reduction because it does not require an organic solvent. In comparison with the conventional fusion process, the method of this invention does not cause melting of the drug and water-soluble polymer and, hence, does not require cooling for solidification and pulverizing of the solid dispersion with the consequent advantages of process simplification and cost reduction.

The solid dispersion obtainable by the production method of this invention and the oral preparation containing the same are superior to the solid dispersion and preparation obtainable by the conventional mixed-grinding process in the solubility of sparingly water-soluble drugs as can be seen clearly from the foregoing Test Examples 1 through 3 and are equivalent to the solid dispersion and preparation obtainable by the conventional solvent process in solubility and bioavailability.

The following examples are intended to describe the invention in further detail.

EXAMPLE 1

A high-speed stir-granulator (Sumitomo Heavy Industries, Ltd.) is charged with nilvadipine (160 g, m.p. 168° C.), hydroxypropylmethylcellulose (800 g, m.p.≧250° C.), low-substituted hydroxypropylcellulose (480 g) and crystalline cellulose (1920 g) and the charge is mixed at a temperature of 155° C. for 1 hour to provide a solid dispersion.

EXAMPLE 2

To the solid dispersion (126 g) of nilvadipine obtained in Example 1 are added lactose (143 g) and magnesium stearate (1 g) and the mixture is molded into tablets each weighing 180 mg in the conventional manner.

EXAMPLE 3

A universal mixer (Shinagawa Kogyosho Co.) is charged with nilvadipine (30 g), hydroxypropylmethylcellulose (150 g), low-substituted hydroxypropylcellulose (90 g) and crystalline cellulose (360 g) and the charge is mixed at 150° C. for 4 hours to provide a solid dispersion.

EXAMPLE 4

A round-bottomed glass beaker is charged with nilvadipine (1 g), polyvinylpyrrolidone (5 g, m.p.≧250° C.), low-substituted hydroxypropylcellulose (3 g) and crystalline cellulose (12 g) and the charge is mixed at 155° C. for 2 hours to provide a solid dispersion.

EXAMPLE 5

A round-bottomed glass beaker is charged with nifedipine (2 g, m.p. 172° C.), hydroxypropylmethylcellulose (10 g) and crystalline cellulose (15 g) and the charge is mixed at 160° C. for 1 hour to provide a solid dispersion.

Production Example 1 (Roll-Mixing Process)

Using a two-roll mixer, a blend of nilvadipine (1 g) and hydroxypropylmethylcellulose (5 g) is mixed for 1 hour to provide a solid dispersion.

Production Example 2 (Ball Mill Mixed-Grinding Process)

Using a ball mill (SPEX Industries), a mixture of nilvadipine (1 g), hydroxypropylmethylcellulose (5 g), low-substituted hydroxypropylcellulose (3 g) and crystalline cellulose (12 g) is mix-ground for 4 hours to provide a solid dispersion.

Production Example 3 (Solvent Process)

To a mixture of hydroxypropylmethylcellulose (100 g), low-substituted hydroxypropylcellulose (300 g) and lactose (477 g) is added a solution of nilvadipine (20 g) in absolute ethanol (550 ml) and after stirring, the ethanol is evaporated in vacuo to provide a solid dispersion.

Production Example 4

To the solid dispersion (598 g) obtained in Production Example 3 is added magnesium stearate (2 g) and the mixture is molded into tablets each weighing 180 mg in the conventional manner.

Production Example 5 (Ball Mill Mixed-Grinding Method)

Using a ball mill (SPEX Industries), a mixture of nifedipine (2 g), hydroxypropylmethylcellulose (10 g) and crystalline cellulose (15 g) is mix-ground for 4 hours to provide a solid dispersion.

What is claimed is:

1. A method for producing a solid dispersion of a sparingly water-soluble drug comprising
    mixing a sparingly water-soluble drug and a water-soluble polymer selected from the group consisting of methylcellulose, ethylcellulose, hydroxyethylcellulose, hydroxypropylcellulose, hydroxypropylmethylcellulose, carboxymethylcellulose, polyvinylpyrrolidone, polyvinyl alcohol, gum arabic, dextrin, gelatin and a mixture thereof together while heating in the absence of an organic solvent,
    at a heating temperature where neither the sparingly water-soluble drug nor the water-soluble polymer are melted, to yield a solid dispersion,
    wherein said mixing is performed by a mixing device selected from the group consisting of a universal mixer and a high-speed stir-granulator; and
    wherein said sparingly water-soluble drug is nilvadipine.

2. The method of claim 1, wherein said heating temperature is 5°–50° C. below the lower of the melting point of said sparingly water-soluble drug and that of said water-soluble polymer.

3. The method of claim 1, wherein said heating temperature is 5°–25° C. below the lower of the melting point of said sparingly water-soluble drug and that of said water-soluble polymer.

4. The method of claim 1, wherein said sparingly water-soluble drug and a water-soluble polymer are mixed together at a sparingly water-soluble drug to water-soluble polymer ratio of from 1:0.5 to 1:10.

* * * * *